(12) United States Patent
Dooney, Jr. et al.

(10) Patent No.: US 10,335,136 B2
(45) Date of Patent: Jul. 2, 2019

(54) TENSIONABLE CONSTRUCTS WITH MULTI-LIMB LOCKING MECHANISM THROUGH SINGLE SPLICE AND METHODS OF TISSUE REPAIR

(71) Applicant: Arthrex, Inc., Naples, FL (US)

(72) Inventors: Thomas Dooney, Jr., Naples, FL (US); Peter J. Dreyfuss, Naples, FL (US); Derek C. Sullivan, Bonita Springs, FL (US); Andrew C. Petry, Naples, FL (US); Paul C. Brady, Knoxville, TN (US); Kyle Chun, Kaneohe, HI (US); Christopher Donaldson, Johnstown, PA (US)

(73) Assignee: Arthrex, Inc., Naples, FL (US)

( * ) Notice: Subject to any disclaimer, the term of this patent is extended or adjusted under 35 U.S.C. 154(b) by 449 days.

(21) Appl. No.: 15/203,953

(22) Filed: Jul. 7, 2016

(65) Prior Publication Data

US 2017/0049434 A1 Feb. 23, 2017

Related U.S. Application Data

(63) Continuation-in-part of application No. 14/831,511, filed on Aug. 20, 2015.

(51) Int. Cl.
*A61B 17/04* (2006.01)
*A61F 2/08* (2006.01)
*A61B 17/06* (2006.01)

(52) U.S. Cl.
CPC ...... *A61B 17/0401* (2013.01); *A61B 17/0485* (2013.01); *A61B 17/06166* (2013.01); *A61B 2017/0403* (2013.01); *A61B 2017/044* (2013.01); *A61B 2017/0412* (2013.01); *A61B 2017/0414* (2013.01); *A61B 2017/0445* (2013.01); *A61B 2017/06185* (2013.01)

(58) Field of Classification Search
CPC ............ A61B 17/0401; A61B 17/0487; A61B 2017/0458; A61B 2017/0445; A61B 2017/0496; A61B 2017/0414; A61B 2017/0412; A61B 2017/0464; A61B 2017/0456; A61B 2017/0427; A61B 2002/0888; A61F 2/0811
See application file for complete search history.

(56) References Cited

U.S. PATENT DOCUMENTS

| 330,087 A | 11/1885 | Binns |
| 2,698,986 A | 1/1955 | Brown |
| 3,176,316 A | 4/1965 | Bodelll |
| 4,099,750 A | 7/1978 | McGrew |
| 4,187,558 A | 2/1980 | Dahlen et al. |
| 4,301,551 A | 11/1981 | Dore et al. |
| 4,400,833 A | 8/1983 | Kurland |

(Continued)

FOREIGN PATENT DOCUMENTS

| DE | 299 10 202 U1 | 9/1999 |
| DE | 201 01 791 U1 | 6/2001 |

(Continued)

*Primary Examiner* — Anh T Dang
(74) *Attorney, Agent, or Firm* — Blank Rome LLP (57) ABSTRACT

Systems and methods for soft tissue to bone repairs, without knot tying. Soft tissue repair systems include self-cinching constructs with a fixation device, a flexible strand with multiple flexible limbs, and a shuttle/pull device attached to the flexible strand to shuttle the multiple flexible limbs through the flexible strand and form a locking splice.

23 Claims, 9 Drawing Sheets

(56) References Cited

U.S. PATENT DOCUMENTS

| | | |
|---|---|---|
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,062,344 A | 11/1991 | Gerker |
| 5,129,902 A | 7/1992 | Goble et al. |
| 5,156,616 A | 10/1992 | Meadows et al. |
| 5,171,274 A | 12/1992 | Fluckiger et al. |
| 5,211,647 A | 5/1993 | Schmieding |
| 5,217,495 A | 6/1993 | Kaplan et al. |
| 5,250,053 A | 10/1993 | Snyder |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,517,542 A | 5/1996 | Huq |
| 5,534,011 A | 7/1996 | Greene, Jr. et al. |
| 5,562,669 A | 10/1996 | McGuire |
| 5,575,819 A | 11/1996 | Amis |
| 5,628,756 A | 5/1997 | Barker et al. |
| 5,643,266 A | 7/1997 | Li |
| 5,645,588 A | 7/1997 | Graf et al. |
| 5,690,676 A | 11/1997 | DiPoto et al. |
| 5,699,657 A | 12/1997 | Paulson |
| 5,931,869 A | 8/1999 | Boucher et al. |
| 5,961,520 A | 10/1999 | Beck et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom et al. |
| 6,517,578 B2 | 2/2003 | Hein |
| 6,533,802 B2 | 3/2003 | Bojarski et al. |
| 6,592,609 B1 | 7/2003 | Bonutti |
| 6,991,636 B2 | 1/2006 | Rose |
| 7,097,654 B1 | 8/2006 | Freedland |
| 7,217,279 B2 | 5/2007 | Reese et al. |
| 7,261,716 B2 | 8/2007 | Strobel et al. |
| 7,320,701 B2 | 1/2008 | Haut et al. |
| 7,494,506 B2 | 2/2009 | Brulez et al. |
| 7,686,838 B2 | 3/2010 | Wolf et al. |
| 7,713,286 B2 | 5/2010 | Singhatat |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,052 B2 | 1/2011 | Kawaura et al. |
| 7,875,057 B2 | 1/2011 | Cook et al. |
| 7,905,903 B2 | 3/2011 | Stone et al. |
| 7,914,539 B2 | 3/2011 | Stone et al. |
| 7,938,847 B2 | 5/2011 | Fanton et al. |
| 8,029,536 B2 | 10/2011 | Sorensen et al. |
| 8,088,130 B2 | 1/2012 | Kaiser et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 8,277,484 B2 | 10/2012 | Barbieri et al. |
| 8,460,322 B2 | 6/2013 | Van Der Burg et al. |
| 8,460,340 B2 | 6/2013 | Sojka et al. |
| 8,652,171 B2 | 2/2014 | Stone et al. |
| 8,652,172 B2 | 2/2014 | Denham et al. |
| 8,758,406 B2 | 6/2014 | Fanton et al. |
| 8,771,315 B2 | 7/2014 | Lunn et al. |
| 8,814,905 B2 | 8/2014 | Sengun et al. |
| 8,821,543 B2 | 9/2014 | Hernandez et al. |
| 8,821,545 B2 | 9/2014 | Sengun |
| 8,932,331 B2 | 1/2015 | Kaiser et al. |
| 8,936,621 B2 | 1/2015 | Denham et al. |
| 2001/0041938 A1 | 11/2001 | Hein |
| 2002/0052629 A1 | 5/2002 | Morgan et al. |
| 2002/0161439 A1 | 10/2002 | Strobel et al. |
| 2003/0114929 A1 | 6/2003 | Knudsen et al. |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0095130 A1 | 5/2006 | Caborn et al. |
| 2006/0142769 A1 | 6/2006 | Collette |
| 2006/0265064 A1 | 11/2006 | Re et al. |
| 2007/0021839 A1 | 1/2007 | Lowe |
| 2007/0083236 A1 | 4/2007 | Sikora et al. |
| 2007/0118217 A1 | 5/2007 | Brulez et al. |
| 2007/0156148 A1 | 7/2007 | Fanton et al. |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0185494 A1 | 8/2007 | Reese et al. |
| 2007/0203508 A1 | 8/2007 | White et al. |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0009904 A1 | 1/2008 | Bourque et al. |
| 2008/0046009 A1 | 2/2008 | Albertorio et al. |
| 2008/0109037 A1 | 5/2008 | Steiner et al. |
| 2008/0140092 A1 | 6/2008 | Stone et al. |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0255613 A1 | 10/2008 | Kaiser et al. |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1 | 3/2009 | Kaiser et al. |
| 2009/0069847 A1 | 3/2009 | Hashiba et al. |
| 2009/0082805 A1 | 3/2009 | Kaiser et al. |
| 2009/0187244 A1 | 7/2009 | Dross |
| 2009/0192546 A1 | 7/2009 | Schmieding et al. |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |

(56) References Cited

U.S. PATENT DOCUMENTS

| | | |
|---|---|---|
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292733 A1 | 11/2010 | Hendricksen et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0071545 A1 | 3/2011 | Pamichev et al. |
| 2011/0087283 A1 | 4/2011 | Donnelly et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053627 A1 | 3/2012 | Sojka et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0089193 A1 | 4/2012 | Stone et al. |
| 2012/0109299 A1 | 5/2012 | Li et al. |
| 2012/0123473 A1 | 5/2012 | Hernandez |
| 2012/0123474 A1 | 5/2012 | Zajac et al. |
| 2012/0123541 A1 | 5/2012 | Albertorio et al. |
| 2012/0130424 A1 | 5/2012 | Sengun et al. |
| 2012/0150297 A1 | 6/2012 | Denham et al. |
| 2012/0158051 A1 | 6/2012 | Foerster |
| 2012/0165867 A1 | 6/2012 | Denham et al. |
| 2012/0165938 A1 | 6/2012 | Denham et al. |
| 2012/0179199 A1 | 7/2012 | Hernandez et al. |
| 2012/0197271 A1 | 8/2012 | Astorino et al. |
| 2012/0239085 A1 | 9/2012 | Schlotterback et al. |
| 2012/0290003 A1 | 11/2012 | Dreyfuss |
| 2012/0296345 A1 | 11/2012 | Wack et al. |
| 2012/0330357 A1 | 12/2012 | Thal |
| 2013/0023928 A1 | 1/2013 | Dreyfuss |
| 2013/0023929 A1 | 1/2013 | Sullivan et al. |
| 2013/0072975 A1 | 3/2013 | Van Der Burg et al. |
| 2013/0085528 A1 | 4/2013 | DiMatteo et al. |
| 2013/0123842 A1 | 5/2013 | Chan et al. |
| 2013/0131723 A1 | 5/2013 | Snell et al. |
| 2013/0144338 A1 | 6/2013 | Stone et al. |
| 2013/0190819 A1 | 7/2013 | Norton |
| 2013/0345749 A1 | 12/2013 | Sullivan et al. |
| 2013/0345750 A1 | 12/2013 | Sullivan |
| 2014/0039551 A1 | 2/2014 | Donahue |
| 2014/0052179 A1 | 2/2014 | Dreyfuss et al. |
| 2014/0121700 A1 | 5/2014 | Dreyfuss et al. |
| 2014/0142627 A1 | 5/2014 | Hendricksen et al. |
| 2014/0257378 A1 | 9/2014 | Norton et al. |
| 2014/0257382 A1 | 9/2014 | McCartney |
| 2014/0257384 A1 | 9/2014 | Dreyfuss et al. |
| 2014/0276992 A1 | 9/2014 | Stone et al. |
| 2015/0045832 A1 | 2/2015 | Sengun |

FOREIGN PATENT DOCUMENTS

| | | |
|---|---|---|
| EP | 0 440 991 A1 | 8/1991 |
| EP | 1 108 401 A1 | 6/2001 |
| EP | 1 707 127 A1 | 10/2006 |
| EP | 2 572 648 A1 | 3/2013 |
| WO | WO 03/022161 A1 | 3/2003 |
| WO | WO 2006/037131 A2 | 4/2006 |
| WO | WO 2007/002561 A1 | 1/2007 |
| WO | WO 2007/109769 A1 | 9/2007 |
| WO | WO 2008/091690 A1 | 7/2008 |

FIG. 8 ns is a continuation-in-part of U.S. application Ser. No. 14/831,511,

TENSIONABLE CONSTRUCTS WITH MULTI-LIMB LOCKING MECHANISM THROUGH SINGLE SPLICE AND METHODS OF TISSUE REPAIR

RELATED APPLICATION

This application is a continuation-in-part of U.S. application Ser. No. 14/831,511, entitled Tensionable Constructs With Multi-Limb Locking Mechanism Through Single Splice and Methods of Tissue Repair, filed Aug. 20, 2015, the subject matter of which is herein incorporated by reference in its entirety.

BACKGROUND

The present invention relates to surgical devices and, in particular, to devices and methods for repair or fixation of soft tissue to bone without the need for knots.

SUMMARY

Surgical constructs, systems, and techniques for knotless soft tissue repair and fixation, such as fixation of soft tissue (ligament, tendon, graft, etc.) to bone are disclosed.

A surgical construct includes a tensionable construct in the form of a multi-limb locking construct formed through a single splice. A flexible strand is split into a plurality of limbs that are shuttled back through a flexible strand, to create a locking splice construct that is tensionable after insertion in bone. A surgical construct allows attached tissue to be brought proximate to bone and does not require tying of any knots. A flexible strand may be fixed to a fixation device and split into a plurality of limbs that are shuttled back through a flexible strand, to create a locking splice construct that is tensionable after insertion in bone.

In an embodiment, a surgical construct includes an anchor, a suture that is attached to the anchor and that splits into two or more limbs, and a suture shuttle with a looped end. A suture can be fixed within the anchor by a knot or similar construct. A suture shuttle is inserted into a center of a single suture with a plurality of suture limbs, to shuttle the suture limbs back through the suture, creating a multi-limb locking mechanism through a single locking splice.

DETAILED DESCRIPTION

Surgical constructs, systems, and techniques for knotless soft tissue repair and fixation, such as fixation of soft tissue (ligament, tendon, graft, etc.) to bone are disclosed.

The surgical constructs comprise tensionable knotless anchors that are inserted into bone and are provided with a multi-limb suture locking mechanism through single splice (tensionable construct). The tensionable knotless anchor may be formed essentially of suture or suture-like material (i.e., a soft anchor without a solid body) or may be attached to a fixation device.

The multi-limb suture locking mechanism through single splice is formed of a flexible strand (a suture) and a shuttle/pull device (a suture passing instrument) attached to the flexible strand. A flexible strand includes an unsplit region or end (a single main limb of suture or main strand) and a plurality of limbs attached to the unsplit region (main strand). A shuttle/pull device attached to the unsplit region allows passing of the plurality of limbs through the tissue and then spliced back through the unsplit region. In this manner, multiple locking limbs with variable loop lengths are locked through just one splice. If a fixation device (such as a solid anchor, for example) is employed, a splice may be formed outside the body of the fixation device or inside the body of the fixation device. A multi-limb suture locking mechanism through single splice may be employed for tissue repairs.

In an embodiment, a flexible strand (for example, suture) is split into multiple strands or limbs. The strands are passed through the tissue and then spliced back through the single main limb of suture. The individual limbs can slide with variable tension and all could lock within the jacket.

In an embodiment, a surgical construct includes an anchor, a suture that is fixed to the anchor and that splits into two or more limbs, and a suture shuttle with a looped end. A suture can be fixed within the anchor by a knot at the end of the suture. A suture shuttle is inserted into a center of the single suture, and is designed to help shuttle the suture limbs back through the suture, creating a single locking splice. A locking splice may be formed outside an anchor body or inside an anchor body.

In another embodiment, a surgical construct comprises (i) a suture or suture-like material that has at least two regions: a first region or unsplit region; and a second region or split region that splits into two or more limbs; and (ii) a suture shuttle with a looped end. A suture shuttle can be pre-assembled to the first region of the suture or suture-like material. A suture shuttle may be inserted into a center of the first region (unsplit region) of the suture or suture-like material. A suture shuttle shuttles the suture limbs back through the suture or suture-like material, creating a single locking splice in the first region (unsplit region) and a plurality of multiple adjustable closed loops. Multiple adjustable closed loops may have adjustable perimeters, and the perimeters may be all similar or different, or at least one perimeter of one loop different than a perimeter of another loop. A surgical construct may consist essentially of (i) a suture or suture-like material that has at least two regions: a first region or unsplit region; and a second region or split region that splits into two or more limbs; and (ii) a suture shuttle with a looped end.

In another embodiment, a surgical construct includes (i) an anchor; (ii) a suture that is fixed to the anchor and that has at least two regions: a first region or unsplit region; and a second region or split region that splits into two or more limbs; and (iii) a suture shuttle with a looped end. A suture can be fixed within the anchor by a knot at the end of the suture. A suture shuttle can be pre-assembled to the first region of the suture. A suture shuttle may be inserted into a center of the first region (unsplit region) of the suture. A suture shuttle shuttles the suture limbs back through the suture, creating a single locking splice in the first region (unsplit region).

In an embodiment, a surgical system for tissue repairs includes a fixation device comprising a body, a longitudinal axis, a proximal end, and a distal end; and a tensionable construct pre-loaded on the fixation device. A tensionable construct may include a flexible strand with a plurality of limbs, and a shuttling device attached to the flexible strand. A flexible strand may have one end which terminates in a knot, and another end which is split into multiple flexible limbs.

Methods of soft tissue repair which do not require tying of knots and allow adjustment of both the tension of the suture and the location of the tissue with respect to the bone are also disclosed. An exemplary method of tissue repair comprises (i) installing a fixation device in bone, the fixation device comprising a body, a flexible strand split into a plurality of multiple flexible limbs, the flexible strand extending through at least a portion of the body of the fixation device, and a passing device attached to the flexible strand; and (ii) forming, with the multiple flexible limbs of the flexible strand and with the passing device, multiple knotless closed loops having adjustable perimeters, after the step of installing the fixation device in bone.

In one embodiment, two or more suture limbs extending from the split suture are passed through soft tissue. The limbs are then inserted into the suture shuttle loop. The tail of the suture shuttle is pulled, advancing the shuttle loop and two or more suture limbs through the locking splice. The ends of each of the two or more suture limbs are then independently advanced until the desired tension is achieved, creating simple stitches along the soft tissue.

In another embodiment, two or more suture limbs, as well as the suture shuttle loop and tail, are all passed through soft tissue. The limbs are then inserted into the suture shuttle loop. The suture shuttle loop and the two or more suture limbs loaded onto it are advanced through the locking splice by pulling the suture shuttle tail. The two or more suture limbs are then independently advanced until the desired tension is achieved, creating a mattress stitch on the soft tissue.

Another exemplary method of soft tissue repair comprises inter alia: (i) inserting a fixation device of a surgical construct into bone, the surgical construct comprising a fixation device (for example, an anchor) with a flexible strand (for example, suture) that is attached to the fixation device and that is split into multiple strands/limbs, and with a shuttle/pull device (a suture passing instrument) attached to the flexible strand; (ii) passing the multiple strands/limbs around or through tissue to be fixated (or reattached) to bone, and then through an eyelet/loop of the shuttle/pull device; and (iii) subsequently, pulling on the shuttle/pull device to allow the multiple strands/limbs to pass through the flexible strand and to form a locking splice. In an embodiment, individual multiple strands/limbs are each advanced until desired tension is achieved creating simple stitches along the tissue. In an embodiment, individual multiple strands/limbs may be sequentially advanced through the flexible strand.

According to another embodiment, a method of soft tissue repair comprises inter alia: (i) inserting a fixation device of a surgical construct into bone, the surgical construct comprising a fixation device (for example, an anchor) with a flexible strand (for example, suture) that is attached to the fixation device and that is split into multiple strands/limbs, and with a shuttle/pull device (a suture passing instrument) attached to the flexible strand; (ii) passing the multiple strands/limbs together with the shuttle/pull device around or through tissue to be fixated (or reattached) to bone; (iii) subsequently, passing the multiple strands/limbs through an eyelet/loop of the shuttle/pull device; and (iv) subsequently, pulling on the shuttle/pull device to allow the multiple strands/limbs to pass through the flexible strand and to form a locking splice. In an embodiment, individual multiple strands/limbs are each advanced until the desired tension is achieved creating a mattress stitch on the tissue. In an embodiment, individual multiple strands/limbs may be sequentially advanced through the flexible strand.

Yet another exemplary method may include the steps of installing at least a first fixation device in bone, the first fixation device comprising a first body and a first flexible strand split into a plurality of limbs; installing at least a second fixation device in bone, the second fixation device comprising a second body and a second flexible strand; passing at least one of the plurality of limbs of the first flexible strand through or around tissue; passing the at least one of the plurality of limbs of the first flexible strand through a portion of the second flexible strand, thereby forming at least a first knotless closed loop having an adjustable perimeter; and adjusting the at least first knotless closed loop to approximate the tissue to bone.

Still yet another exemplary method may include the steps of installing a first fixation device in bone, the first fixation device having a body and a flexible strand split into a plurality of limbs; passing the plurality of limbs through or around tissue; passing the plurality of limbs through the flexible strand thereby forming a plurality of knotless closed loops having adjustable perimeters; and fixing the plurality of limbs to at least one additional fixation device installed in bone after the step of passing the plurality of limbs through the flexible strand forming the plurality of knotless closed loops.

A further exemplary method may include installing a first fixation device in bone, the first fixation device having a body and a flexible strand split into a plurality of limbs; installing a second fixation device in bone, the second fixation device having a body; passing the plurality of limbs through or around tissue; passing at least one of the plurality of limbs through the body of the second fixation device; passing the at least one of the plurality of limbs through the flexible strand thereby forming at least one knotless closed loop having an adjustable perimeter; and adjusting the at least one knotless closed loop to approximate the tissue to bone.

Referring now to the drawings, where like elements are designated by like reference numerals, FIGS. 1-5 illustrate device 100 (surgical construct, integrated system, surgical system, or assembly 100) which includes fixation device 10 assembled with construct 99 (tensionable construct 99) formed of flexible strand or flexible material 30 and shuttle/pull device 40 (suture passing instrument 40) attached to the flexible strand 30. Tensionable construct 99 may be pre-loaded on the fixation device 10. Although the embodiments below will be described with reference to construct 99 (tensionable construct 99) attached to at least a part of fixation device 10, the disclosure is not limited to these exemplary embodiments and contemplates embodiments wherein construct 99 (tensionable construct 99) acts as a soft anchor, i.e., without being attached to any fixation device such as fixation device 10.

In an exemplary embodiment, fixation device 10 is a tensionable knotless anchor having a solid anchor body 11 provided with a longitudinal axis 11a, a proximal end 13, a distal end 12, and a plurality of ribs or ridges 15 extending circumferentially around body 11. Cannulation 11b extends along the body 11 to allow passage of flexible strand 30 and of a suture passing device, as detailed below. Proximal end 13 of the anchor 10 may contain a socket 19 (FIG. 1) configured to securely engage a tip of a driver.

In an exemplary embodiment, fixation device 10 is an anchor 10 which may be a screw-in anchor or a push-in style anchor. Anchor 10 may be formed of metal, biocompatible plastic such as PEEK, or a bioabsorbable PLLA material. Socket 19 at the distal end 13 of the anchor 10 may have any shape adapted to receive a driver tip for pushing tap-in or screw-in style anchors. Anchor 10 may be made of one or more pieces (a multi-piece construct), or may be provided as an integrated device (a unitary device). Anchor 10 may have various sizes (various diameters and/or lengths) and may be formed of biocompatible materials such as PEEK, biocomposite materials, metals and/or metal alloys, or combination of such materials, among others.

In an embodiment, construct 99 (tensionable construct 99) may be formed of flexible strand 30 (flexible material, suture, or tie down suture 30) and shuttle/pull device 40 (suture passing instrument such as FiberLink™ 40, wire loop 40, or nitinol loop 40) attached to the flexible strand 30. In an exemplary embodiment, the flexible strand 30 is a suture strand 30 and the shuttle/pull device 40 is a suture passing device 40. The flexible strand 30 includes an end 32 (unsplit end, unsplit region, or unsplit suture 32) which terminates in knot 31, and another end which is split into multiple limbs 33a, 33b . . . 33n (where "n" may be any number greater than 2). For simplicity, FIGS. 1-5 illustrate flexible strand 30 split into two limbs 33a, 33b; however, the constructs detailed below encompass any number of multiple limbs (suture limbs). Knot 31 may be a static knot 31 which prevents suture 30 from passing through distal blind hole 12a.

Suture 30, which is typically braided or multi-filament or tape, may be preloaded onto the anchor by tying static knot 31 which prevents suture 30 from passing through distal blind hole 12a. The suture may also be preloaded by insert molding or by any other means known in the art. Suture 30 passes through cannulation 11b and terminates in limbs 33a, 33b exiting proximal end 13 of body 11. Tensionable knotless anchor 10 is loaded onto a driver (not shown in FIGS. 1-5), and suture 30 is secured to the driver (for example, wrapped around a cleft of the driver) to fasten tensionable knotless anchor 10 securely to the driver.

Figure 1:
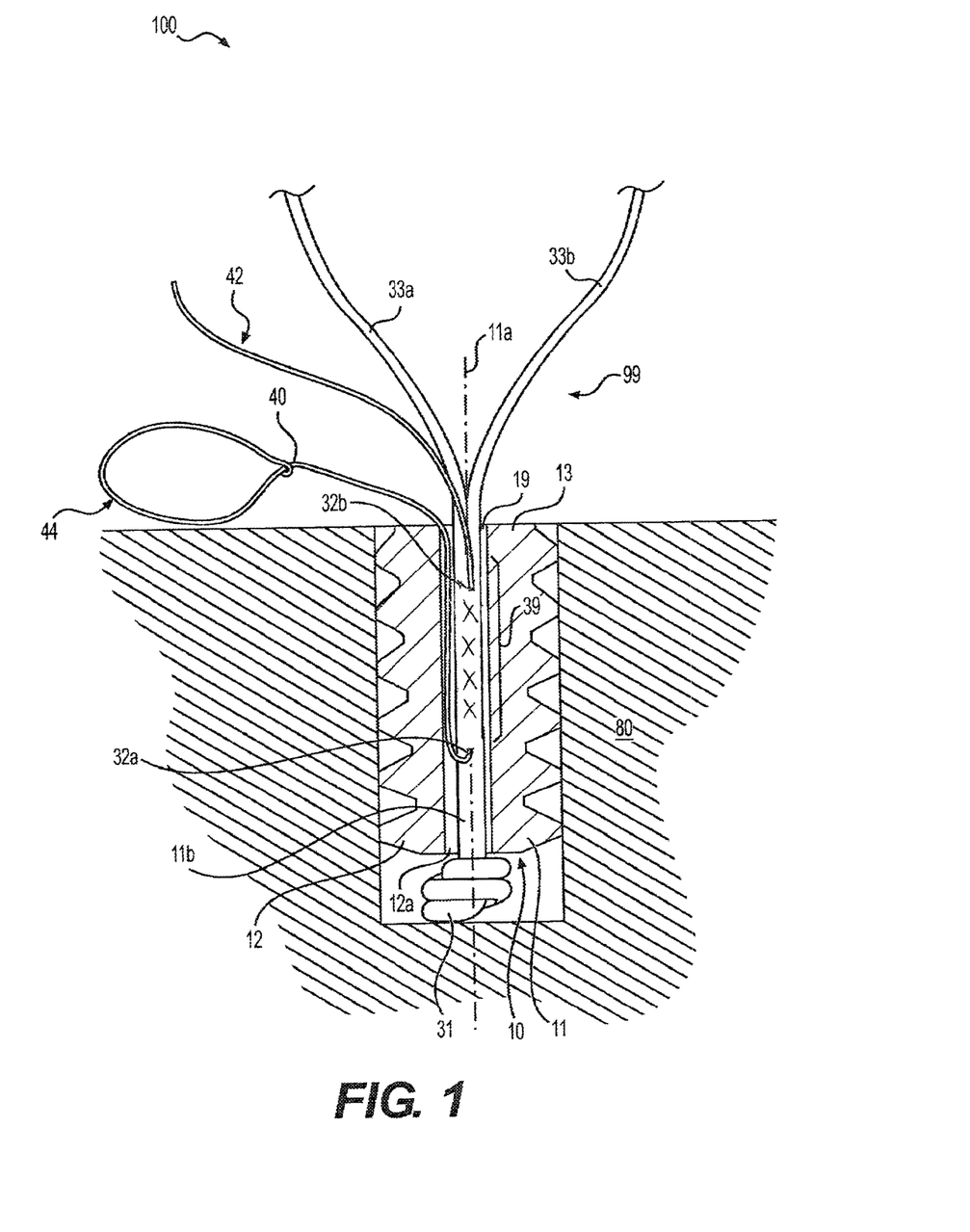
FIG. 1 illustrates a tensionable knotless construct according to an exemplary embodiment.

Prior to the fastening of the anchor 10 to the driver, suture passing device 40 (for example, a FiberLink™, a wire loop, or a nitinol loop) is threaded through suture 30 (i.e., attached to a center of the suture 30 through splice region 39 of unsplit end or region 32), as shown in FIG. 1. Suture passing device 40 includes closed eyelet/loop 44 for passing suture, and tail 42. Suture passing device 40 passes through an aperture 32a of suture 30, within the body of suture 30 and within the tensionable knotless anchor 10, and then exits an aperture 32b of suture 30. A distance between apertures 32a, 32b of suture 30 corresponds to splice or splice region 39. Tensionable knotless anchor 10 loaded with tensionable construct 99 (formed of suture 30 attached to the suture passing device 40) is then secured into bone 80 (for example, into a hole/socket/tunnel formed in bone 80) by using a driver.

Figure 2:
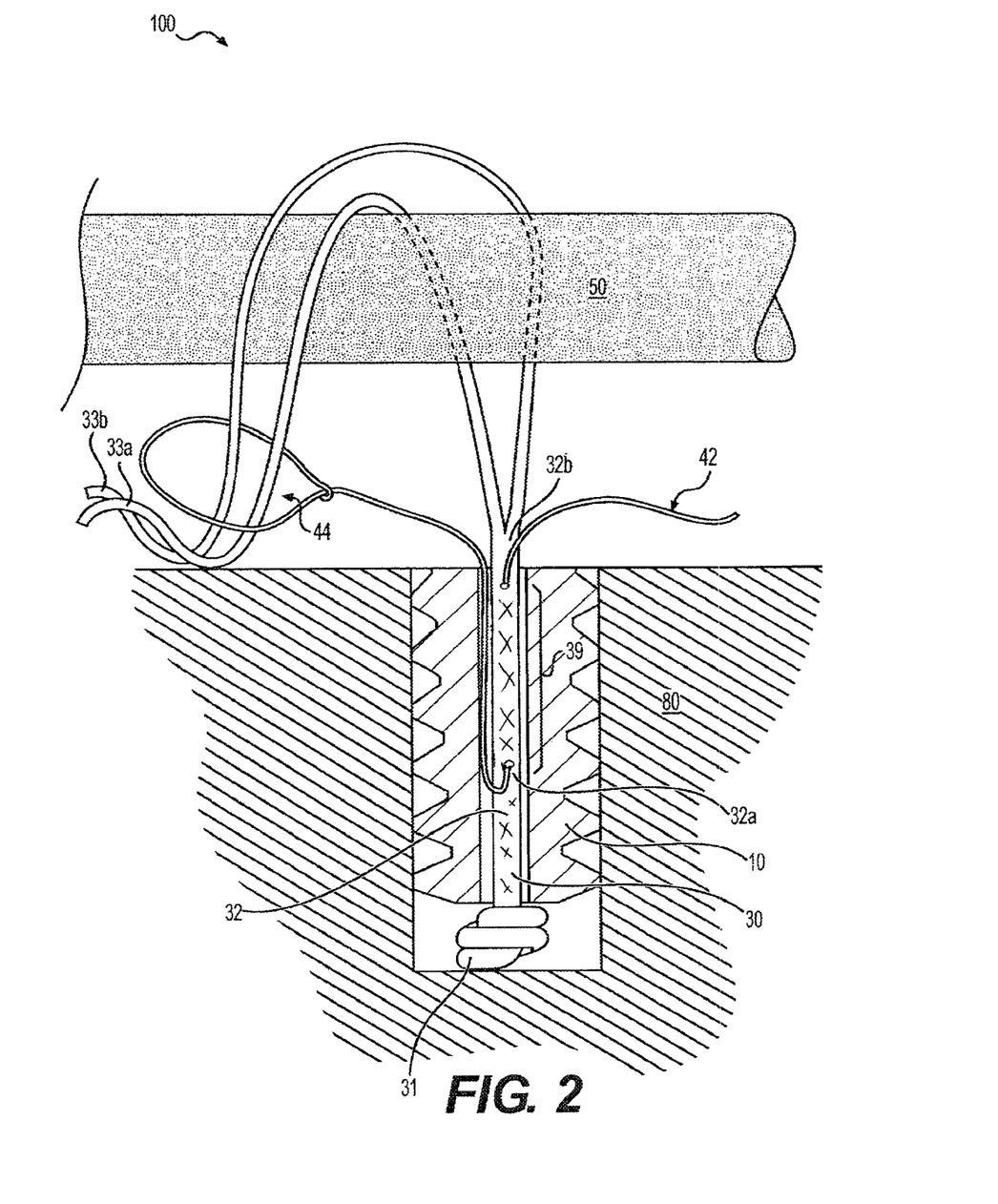
FIGS. 2 and 3 illustrate an exemplary method of tissue repair with the tensionable knotless construct of FIG. 1.
Figure 3:
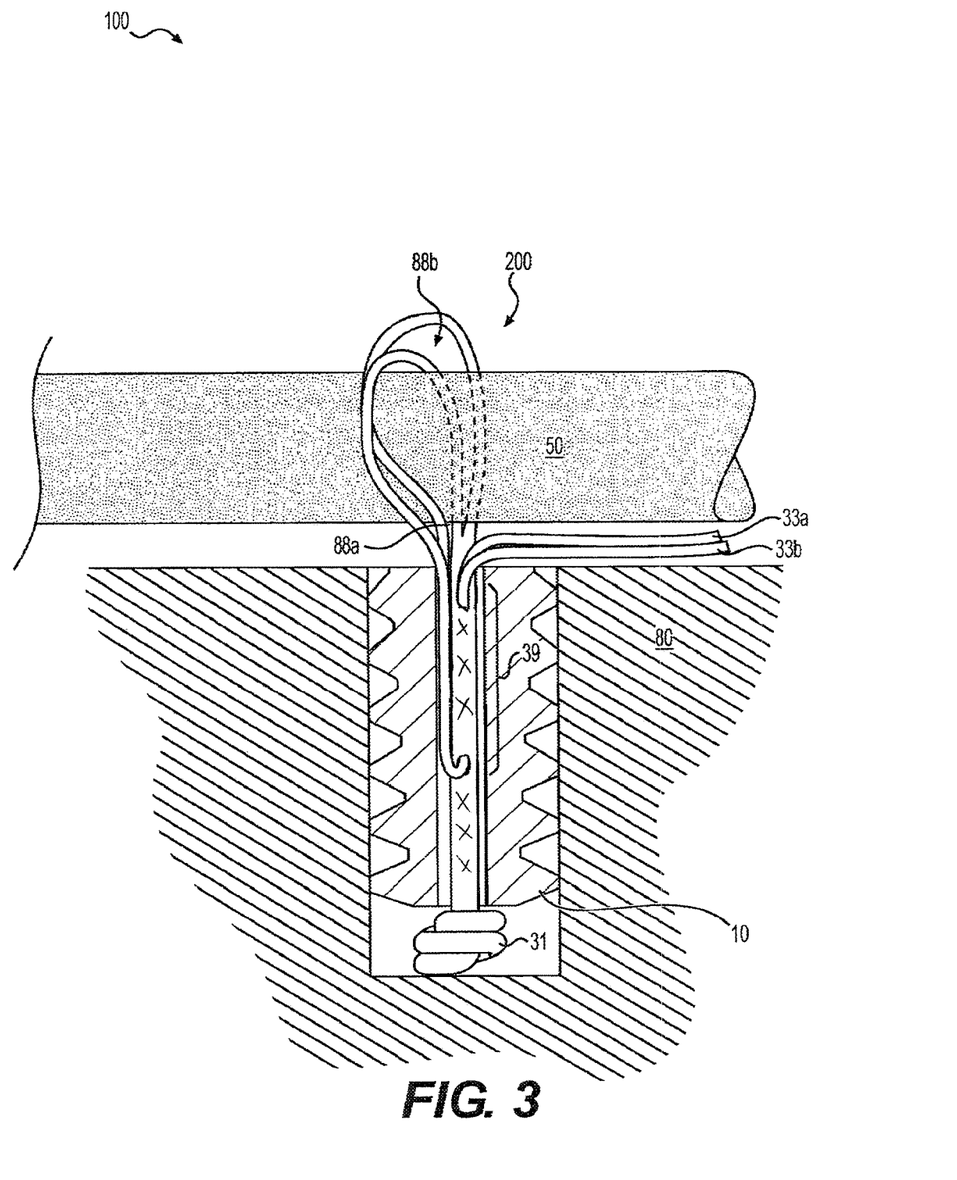

FIGS. 2 and 3 depict exemplary repair 200 with tensionable knotless anchor 10 of construct 100 after it has been inserted into a drilled hole in bone 80, the suture released from the driver, and the driver removed. Suture limbs 33a, 33b are passed through (or around) tissue 50 which is to be moved to a desired location (for example, brought into proximity of a drilled hole or socket in bone 80, to be reattached, for example, to bone 80). Suture limbs 33a, 33b are subsequently passed through eyelet/loop 44 of the suture passing device 40. Tail 42 of suture passing device 40 is then pulled, thereby pulling suture limbs 33a, 33b towards tensionable knotless anchor 10, so that each of the suture limbs 33a, 33b is passed/advanced through locking splice 39 (splice region 39) of suture 30, i.e., each of the suture limbs 33a, 33b doubles on itself within suture 30 and inside tensionable knotless anchor 10, to form multiple adjustable tensionable loops 88a, 88b, . . . 88n (where "n" has any value greater than 2). For simplicity, FIGS. 2 and 3 show only two multiple adjustable loops 88a, 88b corresponding to respective multiple limbs 33a, 33b; however, the constructs disclosed herein contemplate any number of multiple adjustable tensionable loops (corresponding to the number of multiple limbs). The suture passing device 40 has also been further pulled through the splice region 39 of suture 30.

FIG. 3 illustrates surgical construct 100 with limbs 33a, 33b after the limbs have been pulled through themselves, creating locking splice 39 and tensionable loops 88a, 88b. The suture passing device (not visible) helps create single locking splice 39 within tensionable knotless anchor 10 by facilitating suture limbs 33a, 33b of suture 30 to pass through (shuttle back through) the unsplit end or unsplit suture 32. Locking splice 39 may be formed within body 11 of fixation device 10, or outside body 11 of fixation device 10. In an embodiment, locking splice 39 may be formed outside body 11 of fixation device 10 and within a bone tunnel formed within bone 80 (wherein construct 100 is inserted).

Once limbs 33a, 33b have been fully passed through suture 30, each of the limbs 33a, 33b may be pulled to reduce the perimeter of loops 88a, 88b and until tissue 50 has been moved to the desired location, such as near a drilled hole in bone 80. Once the desired tension and location is achieved, ends of limbs 33a, 33b may be clipped off to complete the soft tissue repair or fixation 200.

Figure 4:
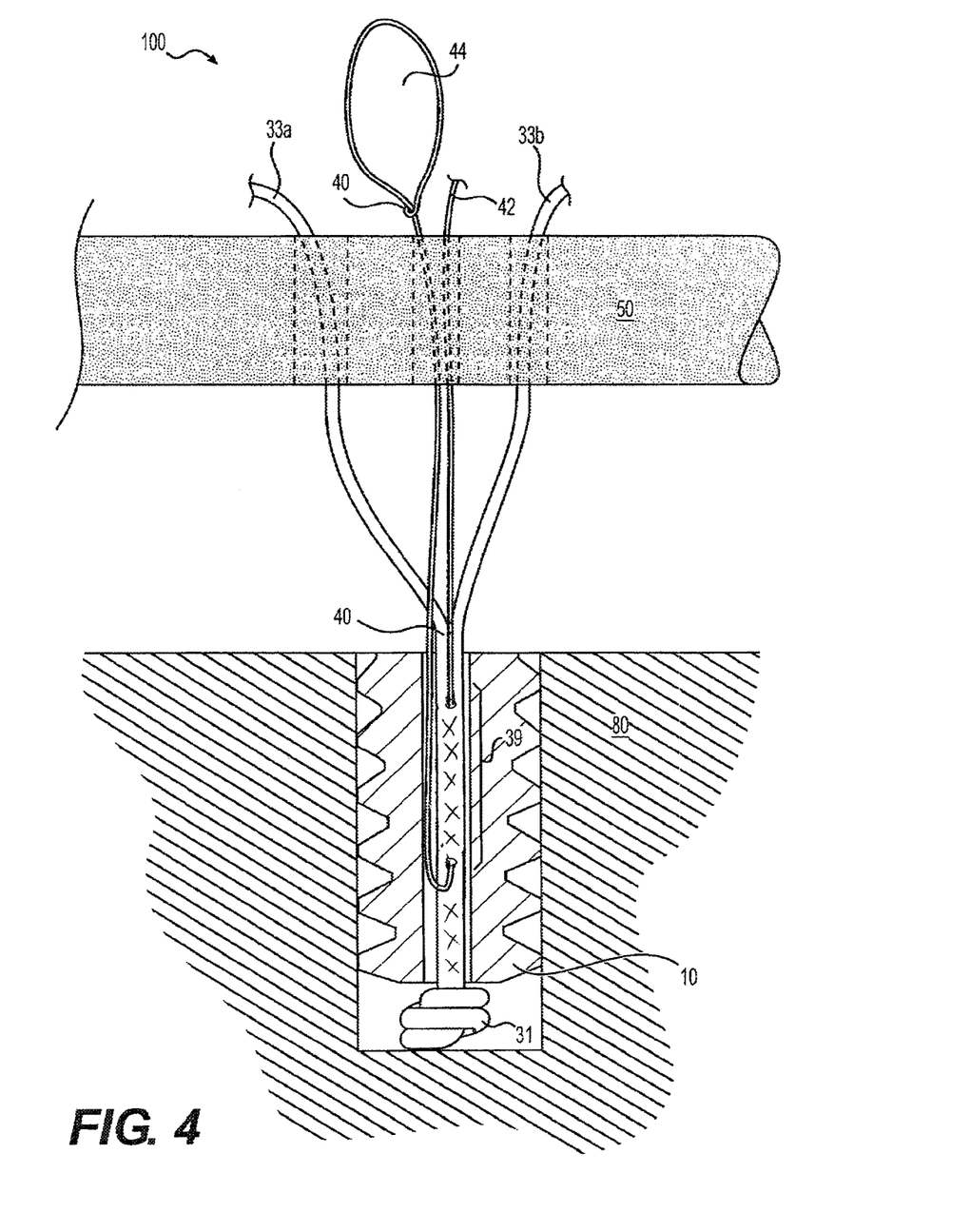
FIGS. 4 and 5 illustrate another exemplary method of tissue repair with the tensionable knotless construct of FIG. 1.
Figure 5:
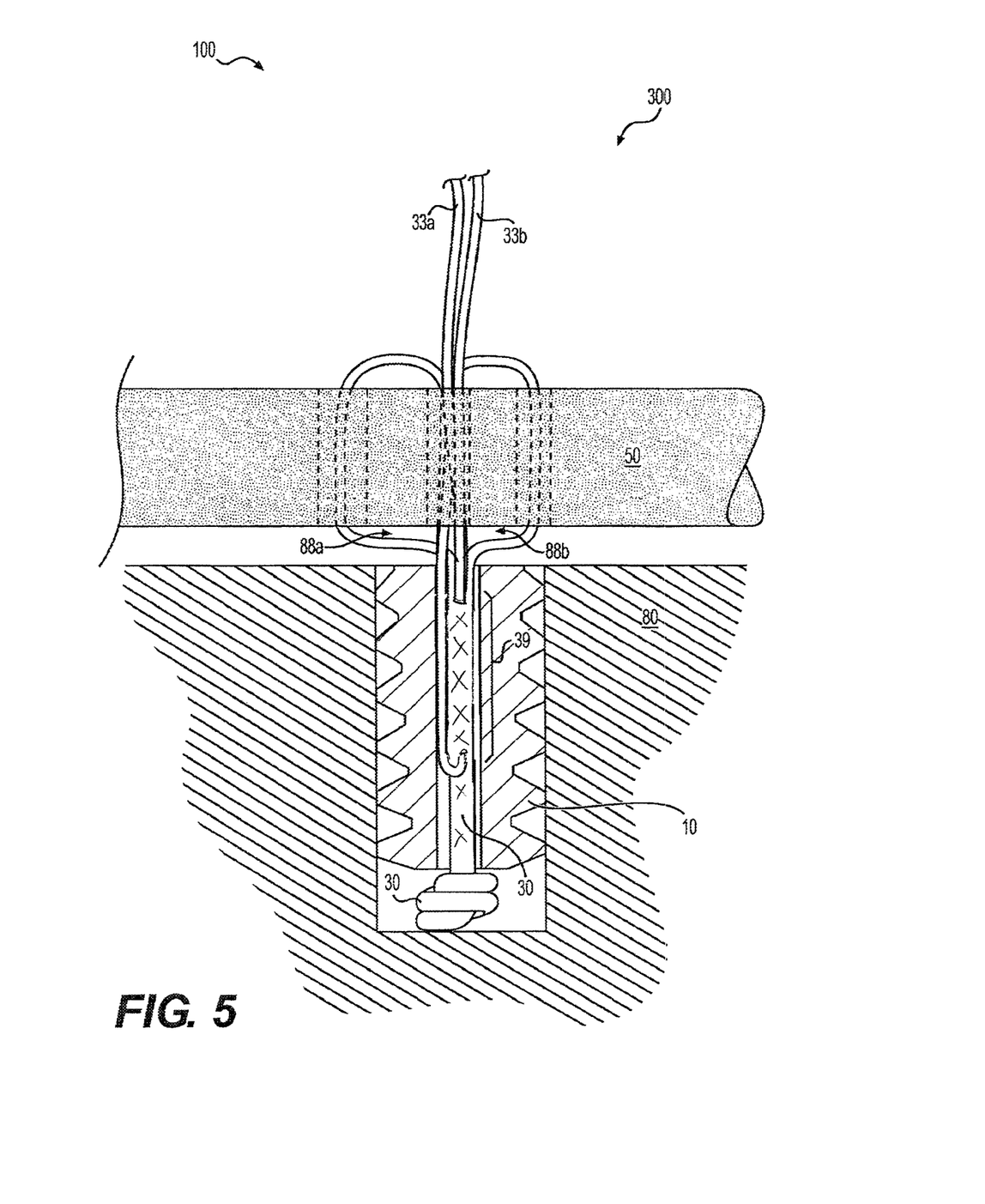

FIGS. 4 and 5 illustrate another exemplary method of soft tissue repair 300 which does not require tying of knots and allows adjustment of both tension of the suture limbs and the location of the tissue with respect to the bone. According to this embodiment, two or more suture limbs 33a, 33b, as well as the suture shuttle loop 44 and tail 42, are all passed through tissue 50. The limbs 33a, 33b are then inserted into the suture shuttle loop 44. The suture shuttle loop 44, together with the two or more suture limbs 33a, 33b loaded onto the suture shuttle loop 44, are advanced through the locking splice 39 by pulling the suture shuttle tail 42, to form adjustable tensionable loops 88a, 88b, as shown in FIG. 5. As in the previously-described embodiment, loops 88a, 88b are multiple adjustable tensionable loops 88a, 88b, each corresponding to a respective one of multiple limbs 33a, 33b. Loops 88a, 88b have an adjustable perimeter and are self-locking, tensionable constructs formed of a splice (spliced region) and a continuous adjustable closed loop attached to the splice. The two or more suture limbs 33a, 33b may be then independently advanced until the desired tension is achieved, creating a mattress stitch on the tissue 50 and completing repair 300. In an embodiment, the two or more suture limbs 33a, 33b may be sequentially or simultaneously advanced, and then independently tensioned so that desired tension is achieved and final repair completed.

Surgical construct 100 with the knotless anchor 10 and tensionable construct 99 may be employed in following exemplary repairs:

1) Used in subscapularis repair for simple partial tears: place anchor 10, pass sutures, shuttle using FiberLoop® (Arthrex, Inc., Naples, Fla.), and tighten.

2) Full rotator cuff (RC) tears (subscapularis, supraspinatus, infraspinatus).
   a. Same technique for single row fixation: this will allow for simple repairs passing only one limb of each suture separately through the RC, then shuttle with FiberLink® (Arthrex, Inc., Naples, Fla.), tighten.
   b. Single row fixation with horizontal mattress: pass sutures separately, pass FiberLink® through RC as well, shuttle sutures, tighten.
   c. Double row fixation with one anchor 10: pass sutures separately, pass FiberLink® through RC, shuttle sutures, tighten, and bring sutures to lateral row anchor(s).
   d. Double row fixation with multiple anchors 10:
      i. Pass sutures/FiberLink® up through RC either as unit or separately as desired; shuttle sutures into opposing anchor with opposing FiberLink® for interconnection medially.
      ii. Since multiple limbs are available, may also shuttle one suture into same anchor for individual anchor fixation. This would be a suture from same anchor/FiberLink® that was passed through RC separately from FiberLink®. This allows for SutureBridge™ fixation without knots.
         1. All passes may be passed through the RC with both anchors done before shuttling sutures.
         2. The technique could feature only two sutures per anchor with two anchors medially and two vented SwiveLock™ (Arthrex, Inc., Naples, Fla.) anchors laterally.

3) Partial Articular-sided Supraspinatus Tendon Avulsion (PASTA) Repair:
   a. Pass anchor 10 through slit in RC or create a sheath to come through the RC easily, then fixate anchor into bone through tendon
   b. Pass sutures separately via Lasso or BirdBeak® (Arthrex, Inc., Naples, Fla.)
   c. Shuttle sutures back into FiberLink®, or if hole too big, shuttle FiberLink® through RC as well into a different, smaller hole
   d. Tighten 4) A tape such as FiberTape® could be incorporated into anchor 10:
   a. This would allow for SpeedBridge™ plus repairs as above to get better fixation and take away that doctors want to "tie" sutures medially to "help with fixation." By interconnecting anchors 10 and passing a suture through the medial tissue, fixing it to its same anchor, surgeons get individual anchor fixation and construct fixation together.
   b. This would also decrease potential for suture cut-through.

5) InternalBrace™—preferably employed with tape. InternalBrace™ may be employed with anchor 10 and interlock anchors across a joint. This would allow a surgeon to "dial in" how much tension to place on the construct. Instead of trying to fix the tension with the initial fixation with the proper length of the FiberTape® (Arthrex, Inc., Naples, Fla.), this technique would allow a surgeon to tighten sequentially. Any external ligament reconstruction or repair like medial collateral ligament (MCL), medial patella-femoral ligament (MPFL), lateral collateral ligament (LCL), anterior cruciate (AC), ankle, etc. would be appropriate. Any internal reconstruction or repair like anterior cruciate ligament (ACL) or posterior cruciate ligament (PCL) could potentially be internally braced with this anchor as well.

6) Any use of a SwiveLock® would be appropriate usage of anchor 10 in lieu of a free suture and vented SwiveLock® (VSL).
   a. This would include ankle or elbow or hip.
   b. SCR would be included in this list as a replacement for VSL.
   c. These could replace the VSL anchors In the SpeedBridge™ kit once the tapes were applied.

Although tensionable knotless anchor 10 has been depicted above having ridges 15, and thus designed to be pushed into bone 80, it could instead be fabricated with threads and thereby designed to be twisted or screwed into bone.

Surgical system 100 of FIGS. 1-5 (with knotless tensionable anchor 10, suture 30 with suture limbs 33a, 33b, and suture passing device 40 attached to suture 30) may be employed in exemplary methods of tissue repair such as a Bankart or SLAP repair, wherein the knotless suture anchor 10 (i.e., a modified knotless SutureTak™ with suture limbs) simplifies arthroscopic glenohumeral joint instability repair by combining a proven and reproducible suture anchor insertion procedure with knotless soft tissue fixation.

Figure 6:
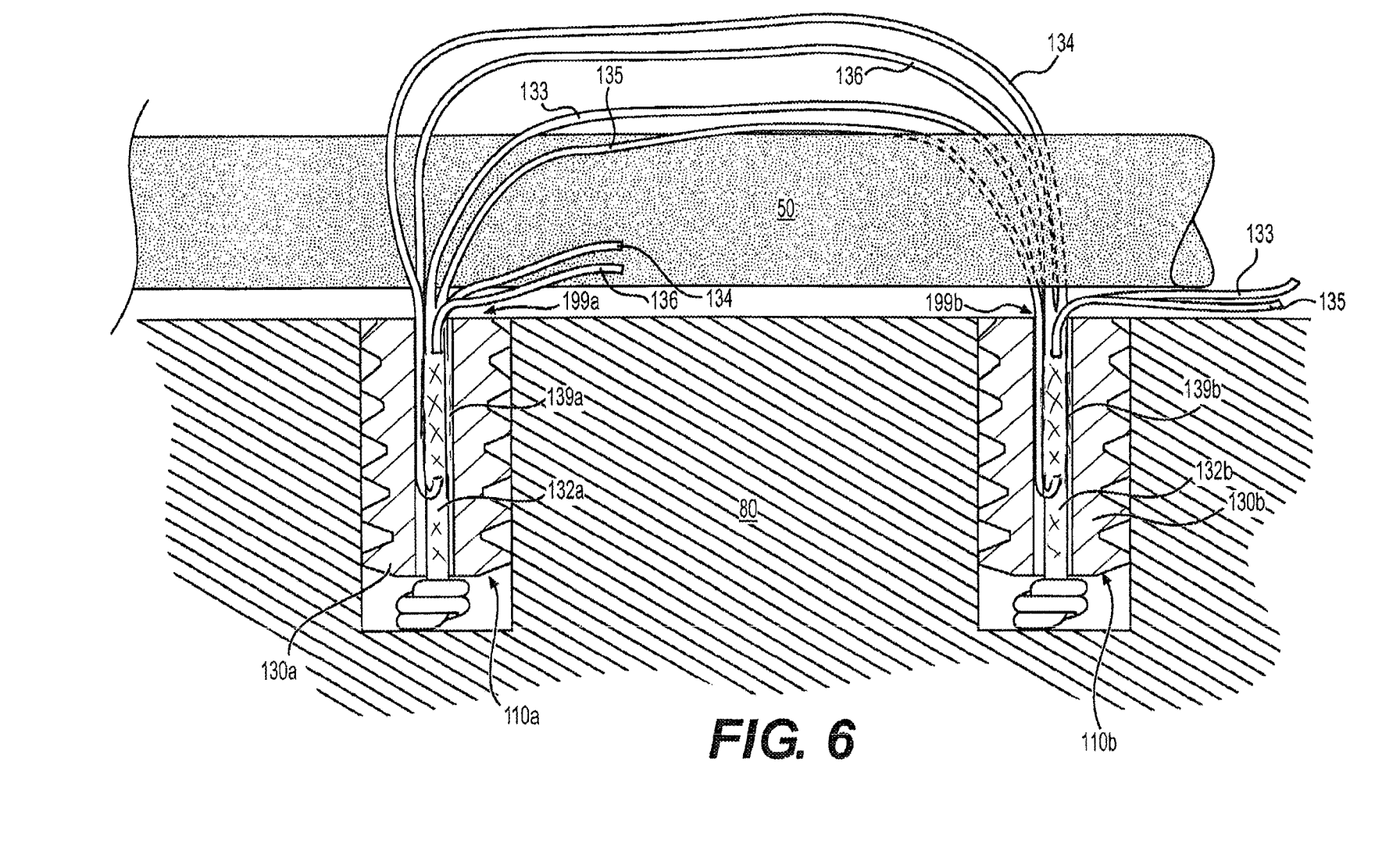
FIG. 6 illustrates yet another exemplary method of tissue repair with two tensionable knotless constructs of FIG. 1.

FIG. 6 illustrates another exemplary method of tissue repair according to the surgical system of the present invention. In this embodiment, first and second fixation devices 110a and 110b are preferably used and installed in bone 80. Fixation devices 110a and 110b may be similar to the fixation devices described in the above embodiments and may each include an anchor body 130a and 130b, respectively, with each preferably being preloaded with a tensionable construct 199a and 199b, respectively. Similar to the tensionable constructs described in the above embodiments, each tensionable construct 199a and 199b may include a flexible strand having an unsplit region 132a and 132b, respectively, and splice region 139a and 139b, respectively, therein. The flexible strand of construct 199a splits into one or more limbs 133 and 135 and the flexible strand of construct 199b splits into one or more limbs 134 and 136. As with the embodiments above, the constructs 199a and 199b may include any number of limbs. In a preferred embodiment, the flexible strands of the constructs 199a and 199b split outside of their respective anchor bodies 130a and 130b.

In the method of FIG. 6, the first and second fixation devices 110a and 110b are installed in bone 80 and spaced from one another such that the one or more limbs 133, 135 of one of the fixation devices 110a can be shuttled through the other fixation device 110b and vice versa, thereby creating locking constructs, like in the embodiments above, in both fixation devices 110a and 110b. The limbs can be shuttled through or around tissue or can go from fixation device to fixation device in any combination. For example, one or more of the limbs 133, 135 of construct 199a may be passed through the splice region 139b of construct 199b, preferably via a passing or shuttling device as described in the embodiments above, thereby forming one or more knotless closed loops having adjustable perimeters. Likewise, one or more of the limbs 134, 136 of construct 199b may be passed through the splice region 139a of construct 199a, thereby forming one or more knotless closed loops. The knotless closed loops may be adjusted and tightened to approximate the tissue 50 to bone 80. The number of limbs leaving each respective fixation device 110a and 110b does not need to equal the number of limbs shuttled back through the respective fixation devices 110a and 110b. More or less limbs could be shuttled into each locking construct of each fixation device 110*a* and 110*b*. Additional fixation devices may be installed in bone 80 that are also preloaded with tensionable constructs. That is, any number of fixation devices with preloaded tensionable constructs may be used in the repair illustrated in FIG. 6 with one or more limbs of each fixation device be shuttled through another construct of another fixation device to form locking constructs.

Figure 7:
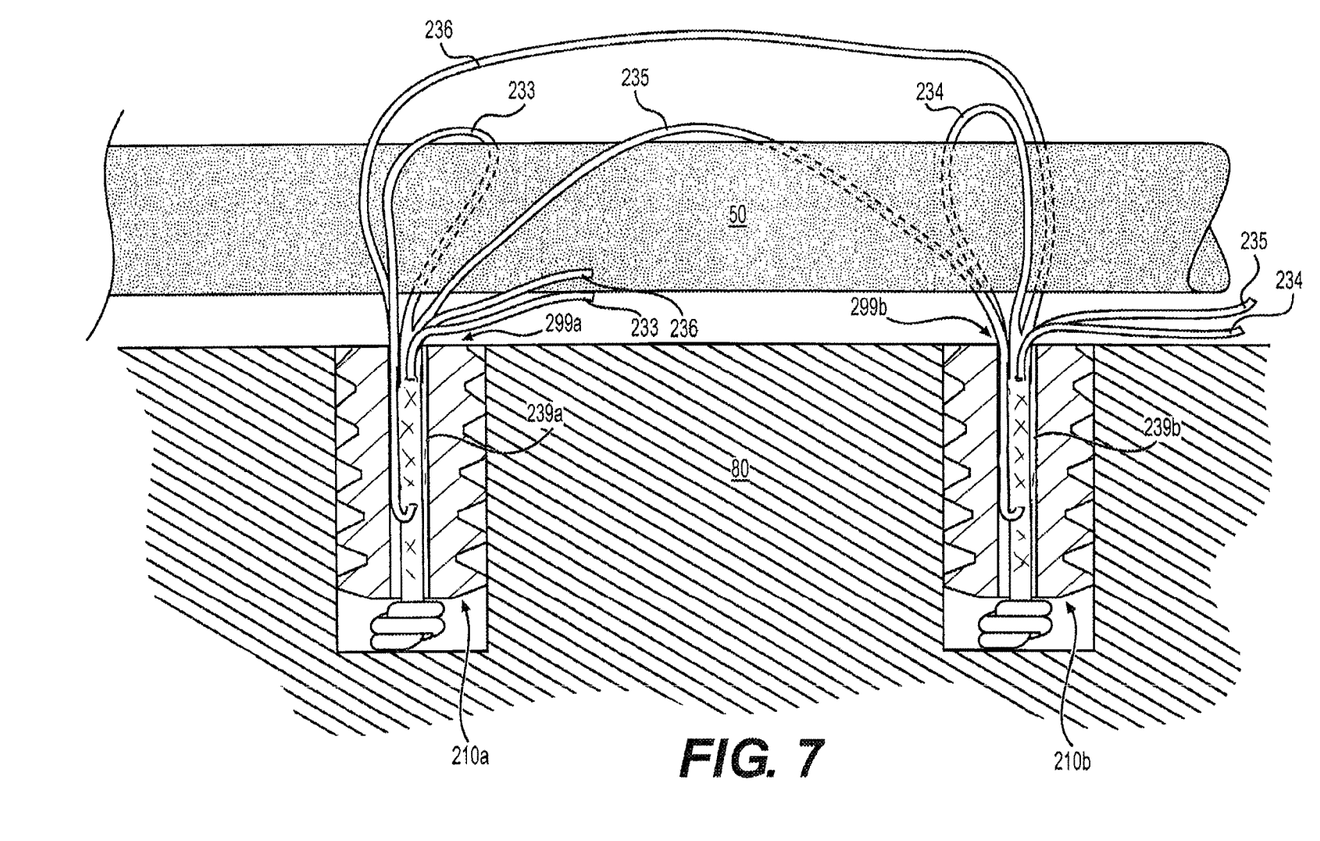
FIG. 7 illustrates still another exemplary method of tissue repair with two tensionable knotless constructs of FIG. 1.

FIG. 7 illustrates yet another exemplary method of tissue repair according to the surgical system of the present invention. Like in the embodiment of FIG. 6, first and second fixation devices 210*a* and 210*b* may be used with preloaded tensionable constructs 299*a* and 299*b*, respectively; however unlike the embodiment of FIG. 6, each construct 299*a* and 299*b* is shuttled through itself and then shuttled through the other construct, creating locking constructs in both fixation devices 210*a* and 210*b*. For example, one limb 233 of construct 299*a* of the first fixation device 210*a* may be shuttled through a splice region 239*a* in itself, thereby forming a locking construct in the first fixation device 210*a*, and the other limb 235 of construct 299*a* may be shuttled through a splice region 239*b* in the other construct 299*b*, thereby forming a locking construct in the second fixation device 210*b*. Likewise, one limb 234 of construct 299*b* of the second fixation device 210*b* may be shuttled through a splice region 239*b* in itself, thereby forming a locking construct in the second fixation device 210*b*, and the other limb 236 of construct 299*b* may be shuttled through a splice region 239*a* of the other construct 299*a*, thereby forming a locking construct in the first fixation device 210*a*. As with the embodiments above, the limbs may pass through or around the tissue 50 and the constructs 299*a* and 299*b* may include any number of limbs to create a respective number of knotless closed loops with adjustable perimeters. The number of limbs leaving each respective fixation device 210*a* and 210*b* does not need to equal the number of limbs shuttled back through the respective fixation devices 210*a* and 210*b*. More or less limbs could be shuttled through their own locking constructs and into each locking construct of each fixation device 210*a* and 210*b*. Any number of additional fixation devices with preloaded tensionable constructs may be used in the repair illustrated in FIG. 7 with one or more limbs of each fixation device be shuttled through themselves and then another construct of another fixation device to form locking constructs.

Figure 8:
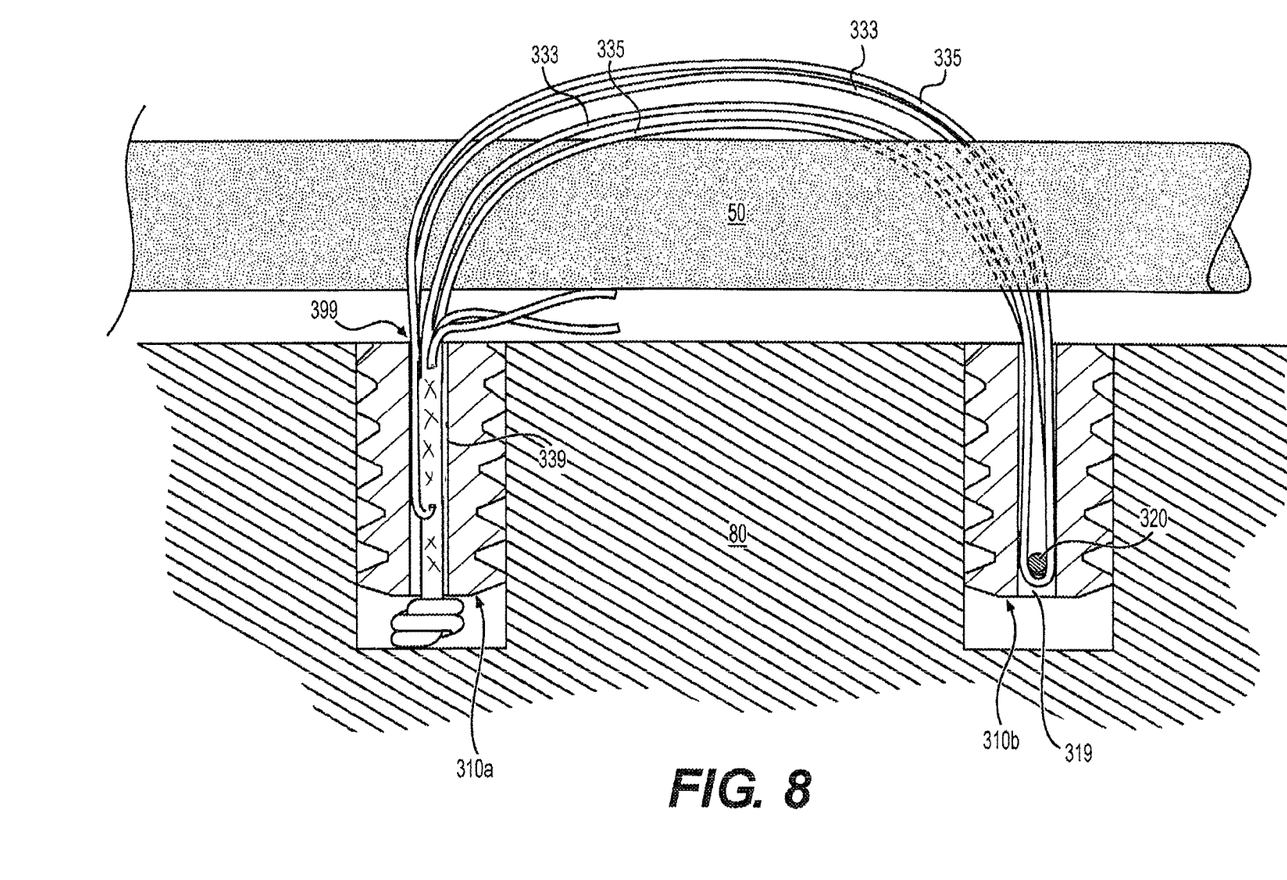
FIG. 8 illustrates still yet another exemplary method of tissue repair with the tensionable knotless construct of FIG. 1.

FIG. 8 illustrates still another exemplary method of tissue repair according to the surgical system of the present invention. In the method of FIG. 8, first and second fixation devices 310*a* and 310*b* are installed in bone 80 with one of the fixation devices 310*a* including a preloaded tensionable construct 399 similar to the constructs of the above embodiments. The second fixation device 310*b* may be different than the first fixation device 310*a* in that it may include a pulley member 320 in a socket 319 of the fixation device 310*b*. One or more limbs 333, 335 of the construct 399 may be passed through or around the tissue 50 and then shuttled through the second fixation device 310*b*, particularly through the socket 319 thereof and around the pulley member 320. After extending around the pulley member 320, the one or more limbs 333 and 335 may then be passed through or around the tissue 50 and then shuttled through a splice region 339 of the flexible strand of the construct 399 to form a locking construct in itself with one or more adjustable closed loops in the same manner as described in the embodiments above. Use of the second fixation device 310*b* expands the reach of the construct 399. The limbs 333 and 335 may be shuttled through or around tissue or can go from fixation device to fixation device in any combination. The construct 399 may include any number of limbs to create a respective number of knotless closed loops with adjustable perimeters. Any number of additional fixation devices with pulley members may be used with the first fixation device 310*a* and construct 399 in the repair illustrated in FIG. 8, with one or more limbs of the construct 399 be shuttled through the pulley members of one or more of the other fixation devices and then form a locking construct in itself.

Figure 9:
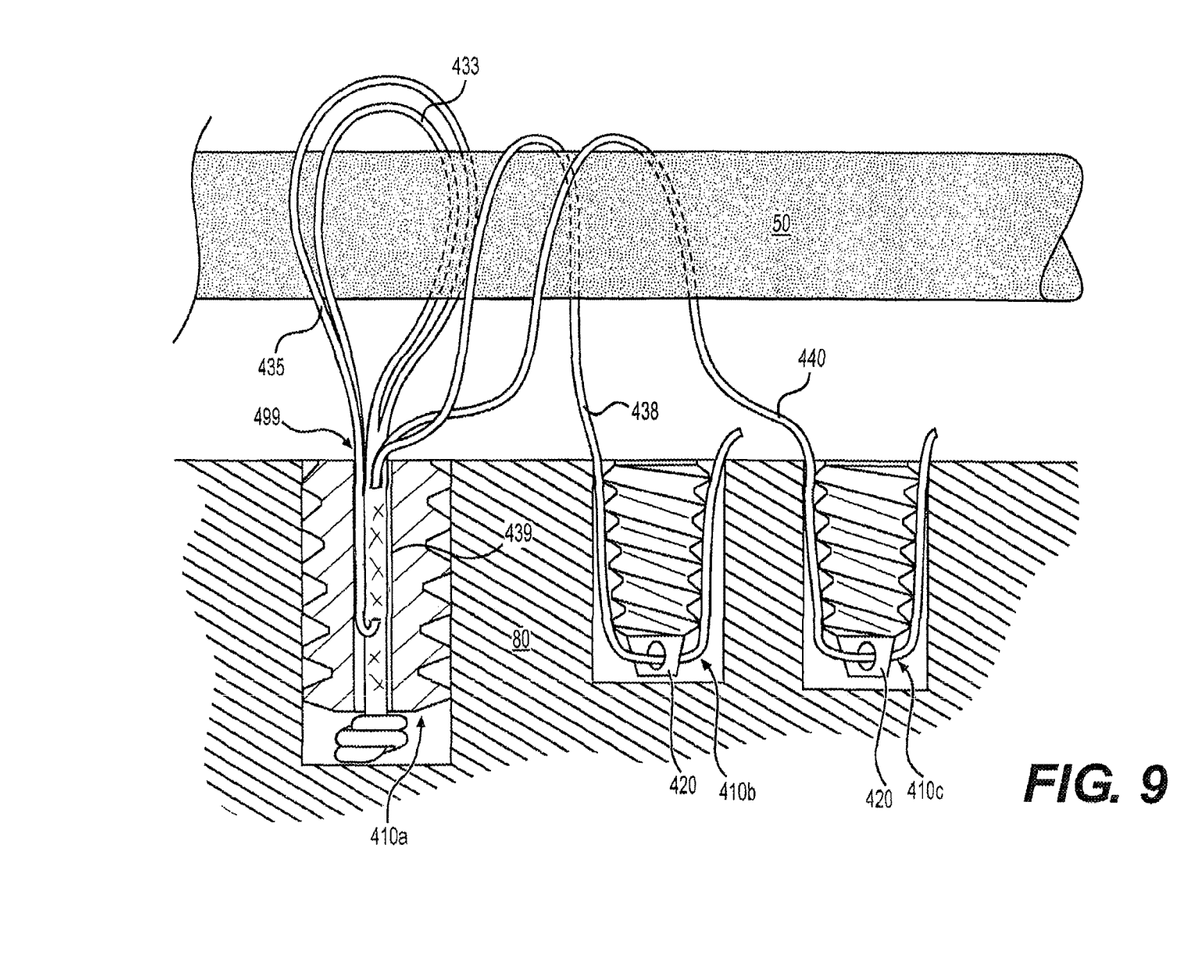
FIG. 9 illustrates a further exemplary method of tissue repair with the tensionable knotless construct of FIG. 1.

FIG. 9 illustrates a further exemplary method of tissue repair according to the surgical system of the present invention. In the method of FIG. 9, the limbs are fixed once the locking construct is created. A first fixation device 410*a* is installed in bone 80 preferably with a preloaded tensionable construct 499 similar to the constructs described in the embodiments above. One or more of the limbs 433 and 435 of the construct 499 may be passed through or around the tissue 50 and shuttled through itself via splice region 439 to form a locking construct in the first fixation device 410*a* with one or more adjustable closed loops, in the same manner as described above. Once the locking construct is created in the first fixation device 410*a*, the free ends 438 and 440 of the limbs 433 and 435, which have already been shuttled through the splice region 439 of the construct 499, may be fixed to second and third fixation devices 410*b* and 410*c* installed in bone 80. For example, the free end 438 of limb 433 may be fixed to the second fixation device 410*b* in a conventional manner and the free end 440 of limb 435 may be fixed to the third fixation device 410*c* in a conventional manner. Alternatively, both free ends 438 and 440 of limbs 433 and 435 may be fixed to one of the second and third fixation devices. Any number of additional fixation devices may be provided to fix the free ends of the one or more limbs 433, 435 of the construct 499. The fixation devices 410*b* and 410*c* may be different than the fixation device 410*a* in that the fixation devices 410*b* and 410*c* preferably include an external eyelet 420 to receive the free end of one or more limbs of the construct 499 to facilitate fixation of the free ends of the construct limbs. The construct 499 may include any number of limbs and one or more of those limbs may be fixed to the second and/or third fixation devices 410*a* and 410*b*.

As with the embodiments above, the limbs of the methods of FIGS. 6-9 are preferably shuttled using a passing or shuttling device. The passing or shuttling device may include one more shuttle loops that receive the limbs to facilitate shuttling of the limbs through the tensionable constructs to form the locking constructs with adjustable closed loops. The limbs from a preloaded fixation device may be split to shuttle the limbs thereof back through the construct of that fixation device in various locations to form the locking construct. The limbs of the constructs from a fixation device can be spliced together into one tail for easy suture management. The flexible strand of the construct can be split to create two separate splices to be used with the separate limbs or additional flexible strand to be incorporated into the repair. The limbs can be passed through multiple separate segments of tissue through repeated passes to approximate the tissue together.

The knotless suture constructs and systems detailed above may be used in conjunction with any knotless fixation devices which can allow a flexible strand and attached suture passing device to form a single locking splice with attached multiple adjustable loops formed by multiple suture limbs. The knotless suture constructs and systems detailed above may be used in conjunction with any additional fixation devices (which may be similar to or different from construct 100) depending on the characteristics of the repair site.

A flexible strand may be a suture strand, a tape such as suture tape, or any suture-like material known in the art that could pass through tissue. A flexible strand may include a high-strength suture, such as an ultrahigh molecular weight polyethylene (UHMWPE) suture. High strength suture may be a FiberWire® suture (Arthrex). FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material.

A flexible strand may be also formed of TigerWire® suture, or suture chain (such as FiberChain® disclosed in U.S. Pat. No. 7,803,173), or suture tape (such as FiberTape® disclosed in U.S. Pat. No. 7,892,256), the disclosures of which are all incorporated in their entireties herein.

At least one of a flexible strand and a shuttle/pull device may be made of any known suture material, such as UHMWPE material or the FiberWire® suture. The UHWMPE suture may be without a core to permit ease of splicing. The shuttle/pull device may be a shuttle/pull suture device such as a FiberLink™ or a Nitinol loop.

The limbs may also be formed of a flexible material, a stiff material, or combination of stiff and flexible materials, depending on the intended application. Both the limbs and the splice region may be also coated and/or provided in different colors. The knotless anchors of the present invention can be used with any type of flexible material or suture that forms a splice and a loop.

What is claimed is:

1. A method of tissue repair, comprising the steps of:
    installing at least a first fixation device in bone, the first fixation device comprising a first body and a first flexible strand comprising an unsplit end and an opposite split end, the split end being split into a plurality of limbs;
    installing at least a second fixation device in bone, the second fixation device comprising a second body and a second flexible strand;
    passing at least one of the plurality of limbs of the first flexible strand through or around tissue;
    passing the at least one of the plurality of limbs of the first flexible strand of the first fixation device through a portion of the second flexible strand of the second fixation device, thereby forming at least a first knotless closed loop having an adjustable perimeter; and
    adjusting the at least first knotless closed loop to approximate the tissue to bone.

2. The method of claim 1, wherein the portion of the second flexible strand is a splice region.

3. The method of claim 2, wherein the step of forming the at least first knotless closed loop further comprises using a first passing device coupled to the first flexible strand, the first passing device having at least one shuttle loop to pass the at least one of the plurality of limbs of the first flexible strand through the splice region of the second flexible strand, thereby forming a locking splice within the second flexible strand.

4. The method of claim 1, further comprising the step of passing at least another one of the plurality of limbs of the first flexible strand through a portion of the first flexible strand, thereby forming another knotless adjustable closed loop having an adjustable perimeter.

5. The method of claim 4, wherein the portion of the first flexible strand is a splice region.

6. The method of claim 1, further comprising the step of passing at least another one of the plurality of limbs of the first flexible strand through a portion of the second flexible strand, thereby forming another knotless adjustable closed loop having an adjustable perimeter.

7. The method of claim 1, further comprising the step of passing the at least one of the plurality of limbs through multiple separate segments of the tissue through repeated passes to approximate the tissue segments together.

8. The method of claim 1, wherein the second flexible strand splits into a plurality of limbs; and further comprising the steps of:
    passing at least one of the plurality of limbs of the second flexible strand through or around the tissue;
    passing the at least one of the plurality of limbs of the second flexible strand through a portion of the first flexible strand, thereby forming at least a second knotless closed loop having an adjustable perimeter; and
    adjusting the at least a second knotless closed loop to approximate the tissue to bone.

9. The method of claim 8, wherein the step of forming the at least a second knotless closed loop further comprises using a second passing device coupled to the second flexible strand, the second passing device having at least one shuttle loop to pass the at least one of the plurality of limbs of the second flexible strand through the first flexible strand, thereby forming a locking splice within the first flexible strand.

10. The method of claim 8, further comprising the step of passing at least another one of the plurality of limbs of the second flexible strand through a portion of the second flexible strand, thereby forming another knotless adjustable closed loop having an adjustable perimeter.

11. The method of claim 10, wherein the step of forming the plurality of first knotless closed loops further comprises using a passing device coupled to the first flexible strand, the passing device having at least one shuttle loop to pass the plurality of limbs of the first flexible strand through the second flexible strand, thereby forming a locking splice within the second flexible strand.

12. The method of claim 8, further comprising the step of passing at least another one of the plurality of limbs of the first flexible strand through a portion of a third flexible strand of a third fixation device installed in bone, thereby forming another knotless adjustable closed loop having an adjustable perimeter.

13. The method of claim 1, further comprising the steps of passing each of the plurality of limbs of the first flexible strand through or around the tissue; and passing each of the plurality of limbs of the first flexible strand through a portion of the second flexible strand, thereby forming a plurality of first knotless closed loops each having an adjustable perimeter.

14. The method of claim 1, wherein the first flexible strand splits into the plurality of limbs outside of the body of the first fixation device.

15. A method of tissue repair, comprising the steps of:
    installing a first fixation device in bone, the first fixation device having a body and a flexible strand that comprises an unsplit end and an opposite split end, the split end being splits into a plurality of limbs;
    passing the plurality of limbs through or around tissue;
    passing the plurality of limbs through the flexible strand thereby forming a plurality of knotless closed loops having adjustable perimeters; and fixing free ends of the plurality of limbs of the first fixation device to at least one additional fixation device installed in bone after the step of passing the plurality of limbs through the flexible strand forming the plurality of knotless closed loops.

16. The method of claim 15, further comprising the step of preloading the first fixation device with the flexible strand and a passing device coupled to the flexible strand, the passing device having at least one shuttle loop for passing the plurality of limbs through the flexible strand, thereby forming a locking splice in the flexible strand.

17. The method of claim 15, wherein each of the free ends of each of the plurality of limbs is fixed to at least one additional fixation device, respectively.

18. The method of claim 15, wherein each of the additional fixation devices includes an external eyelet that receives each of the free ends of the plurality of limbs, respectively.

19. A method of tissue repair, further comprising the steps of:
    installing a first fixation device in bone, the first fixation device having a body and a flexible strand that comprises an unsplit end and an opposite split end, the split end being splits into a plurality of limbs;
    installing a second fixation device in bone, the second fixation device having a body;
    passing the plurality of limbs through or around tissue;
    passing at least one of the plurality of limbs of the first fixation device through the body of the second fixation device;
    passing the at least one of the plurality of limbs through the flexible strand thereby forming at least one knotless closed loop having an adjustable perimeter; and
    adjusting the at least one knotless closed loop to approximate the tissue to bone.

20. The method of claim 19, wherein the step of forming the knotless closed loop further comprises using a passing device coupled to the flexible strand, the passing device having at least one shuttle loop to pass the at least one of the plurality of limbs through the second fixation device, and through the flexible strand, thereby forming a locking splice within the flexible strand.

21. The method of claim 20, passing at least another one of the plurality of limbs through either the second fixation device or a third fixation device, and through the flexible strand to form another knotless closed loop that has an adjustable perimeter.

22. The method of claim 20, wherein the second fixation device is different than the first fixation device.

23. The method of claim 22, wherein the second fixation device includes a pulley member in a socket thereof, and the at least one of the plurality of limbs passes around the pulley member.

* * * * *